(12) United States Patent
Ambardekar

(10) Patent No.: US 8,608,764 B2
(45) Date of Patent: Dec. 17, 2013

(54) DISPOSABLE AND REUSABLE MORCELLATOR

(76) Inventor: Sandeep Ambardekar, Mumbai (IN)

( * ) Notice: Subject to any disclaimer, the term of this patent is extended or adjusted under 35 U.S.C. 154(b) by 113 days.

(21) Appl. No.: 13/146,377

(22) PCT Filed: Feb. 3, 2010

(86) PCT No.: PCT/IN2010/000063
§ 371 (c)(1),
(2), (4) Date: Jul. 26, 2011

(87) PCT Pub. No.: WO2010/089777
PCT Pub. Date: Aug. 12, 2010

(65) Prior Publication Data
US 2011/0282374 A1    Nov. 17, 2011

(30) Foreign Application Priority Data

Feb. 4, 2009   (IN) .......................... 220/MUM/2009
Jan. 28, 2010  (IN) .......................... 222/MUM/2010

(51) Int. Cl.
*A61B 17/32*   (2006.01)
*A61B 17/00*   (2006.01)

(52) U.S. Cl.
USPC ............................................. 606/170; 606/79

(58) Field of Classification Search
CPC ................ A61B 17/320068; A61B 17/32002; A61B 17/320016; A61B 17/14; A61B 17/32053
USPC ......... 606/169, 170, 171, 175, 176, 178, 179, 606/180

See application file for complete search history.

(56) References Cited

U.S. PATENT DOCUMENTS

| 5,133,729 | A | * | 7/1992 | Sjostrom ....................... 606/180 |
| 5,275,607 | A | * | 1/1994 | Lo et al. ........................ 606/169 |
| 5,437,678 | A | * | 8/1995 | Sorensen ....................... 606/107 |
| 5,490,860 | A | * | 2/1996 | Middle et al. ................. 606/171 |
| 5,814,044 | A |   | 9/1998 | Hooven |
| 5,858,007 | A | * | 1/1999 | Fagan et al. ................... 604/256 |
| 6,022,363 | A |   | 2/2000 | Walker et al. |
| 6,039,748 | A |   | 3/2000 | Savage et al. |
| 2006/0200153 | A1 | | 9/2006 | Harp |
| 2008/0039884 | A1 | | 2/2008 | Nohilly et al. |

FOREIGN PATENT DOCUMENTS

EP   1256319 A2   11/2002

OTHER PUBLICATIONS

International Search Report issued in PCT/IN2010/000063 on Aug. 20, 2010.

* cited by examiner

*Primary Examiner* — Tuan V Nguyen
(74) *Attorney, Agent, or Firm* — Blank Rome LLP

(57) ABSTRACT

Provided is an improved morcellator for severing and removing tissue from a patient's body with functional and structural improvements in disposable cutter assembly and reusable drive assembly to prevent body fluid from entering the sterile region of the cutter assembly and infection from transmitting to reusable drive assembly.

9 Claims, 11 Drawing Sheets

DISPOSABLE AND REUSABLE MORCELLATOR

This application is a U.S. national phase of International Patent Application No. PCT/IN2010/000063, filed on Feb. 3, 2010, which claims the benefit of Indian Patent Application No. 220/MUM/2009, filed Feb. 4, 2009 and Indian Patent Application No. 222/MUM/2010, filed Jan. 28, 2010.

FIELD OF THE INVENTION

The present invention in general relates to the field of surgical devices. More particularly the invention provides an improved morcellator for severing and removing tissue from a patient's body.

BACKGROUND OF THE INVENTION

Laparoscopic surgery also referred as minimally invasive surgery, bandaid surgery, keyhole surgery is commonly and widely accepted method of doing surgical procedures. Generally, these laparoscopic surgical procedures make use of one or more small incisions to access internal tissues, often through a cannula, trocar, or other surgical device. The popularity of laparoscopic procedure facilitated surgeons to perform complex surgeries with number of advantages to the patient such as less complication, less blood loss, smaller incisions, shorter recovering time and overall low cost.

Unfortunately, many surgical procedures involving removal of relatively, large masses of tissue, for example, removal of uterus, fibroid, or the like are difficult to accomplish through laparoscopic cannulas or other surgical devices. Removing such large tissue masses laparoscopically through a small access lumen is fairly difficult and time consuming.

Specialized devices have lately developed to sever large tissue masses into segments, which are more easily removed using laparoscopic surgery. These devices generally include a rotating tube having a sharpened distal end which extends through a fixed outer tube. This sharpened end is inserted into the patient through a cannula, or directly through an incision. The surgeon inserts a forceps through the rotating tube. Grasping the large mass of tissue to be removed, the surgeon pulls the tissue up into the tube, so that the rotating edge severs the grasped portion from the large mass. The size of the severed tissue is generally limited by the outline of the rotating edge, so that the surgeon can continue to pull the severed tissue out of the patient through the rotating tube. By repeating the grasping and severing procedure, surgeons can remove relatively large masses of tissue quite quickly. As the large tissue mass is removed in small, individually grasped morcels, these devices are often referred to as "morcellators".

Morcellators are either single use disposable or reusable. However, the reusable morcellators carry of risk of cross infection from one patient to another if not sterilized properly. In addition, there are no specific tests or measures to ensure 100% sterility of these re-sterilized devices. Also, sterilizing these devices is fairly time consuming and so expensive.

Single use disposable morcellators are costly as whole morcellator is required to be disposed after surgery. Disposing off large amount of plastic and metal also leads to environmental pollution, wastage and significant cost put pressure on the healthcare system.

In the light of the above, it would be desirable to provide improved and cost-effective methods and devices for severing and removing tissue from a patient's body.

SUMMARY OF THE INVENTION

In accordance with the present invention there is provided an improved morcellator, which prevents infection from transmitting to reusable parts of the morcellator. The morcellator comprises a disposable cutter assembly and a reusable drive assembly. In addition, the improved morcellator of the present invention provides various functional and structural features in the reusable drive assembly and the disposable cutter assembly which prevents body fluid from entering the sterile region of the cutter assembly and infection from transmitting to the reusable drive assembly.

The improved morcellator includes a rotary tissue cutting tube, which passes through an outer sheath tube and is driven by a cutter gear mechanism of the cutter assembly, and the reusable drive assembly. A hydraulic seal is attached each at a distal and proximal end of the cutter assembly to maintain a sterile region between the distal and proximal end of the cutter assembly and preventing blood/body fluid from entering into the sterile region.

The reusable drive assembly includes a drive gear mechanism. A Hydraulic seal is provided in the drive gear mechanism below the pinion gear for preventing a body fluid or an infection seeping into the drive assembly. In addition, the reusable drive assembly may have protrusions designed over an integrated lever to facilitate proper and firm positioning of the drive assembly when attached to the cutter assembly.

In one embodiment of the present invention there is provided a rotary tissue cutting tube with improved cutter profile designed to facilitate low drag of forceps during tissue removal from the patient's body. The improved tissue cutting tube is variable in diameter and having a cutting edge with double shear angle.

In another embodiment of the present invention there is provided a cutter activation mechanism designed to prevent unintentional exposure of the rotary tissue cutting tube by controlling the movement of outer sheath tube. The cutter activation mechanism includes a pull collar and two locking slots. The cutter activation mechanism provides safe functioning of the morcellator.

In yet another embodiment of the present invention there is provided improved valve designed to facilitate low drag of forceps during tissue removal from the patient's body. The valve consists of two membranes, wherein first membrane is made of single material having uniform elasticity, and second membrane is partly made of a composite or a fused material having variable elasticity and partly made of a non-elastic material.

The present invention, including its embodiments and other features, will become more apparent from the following detailed description with reference to the accompanying drawings.

BRIEF DESCRIPTION OF THE DRAWING

The present invention may best be understood by reference to the following description, taken in connection with the accompanying drawings in which the reference numerals designate like parts throughout the figures thereof and wherein.

DETAILED DESCRIPTION OF PREFERRED EMBODIMENTS

Figure 1:
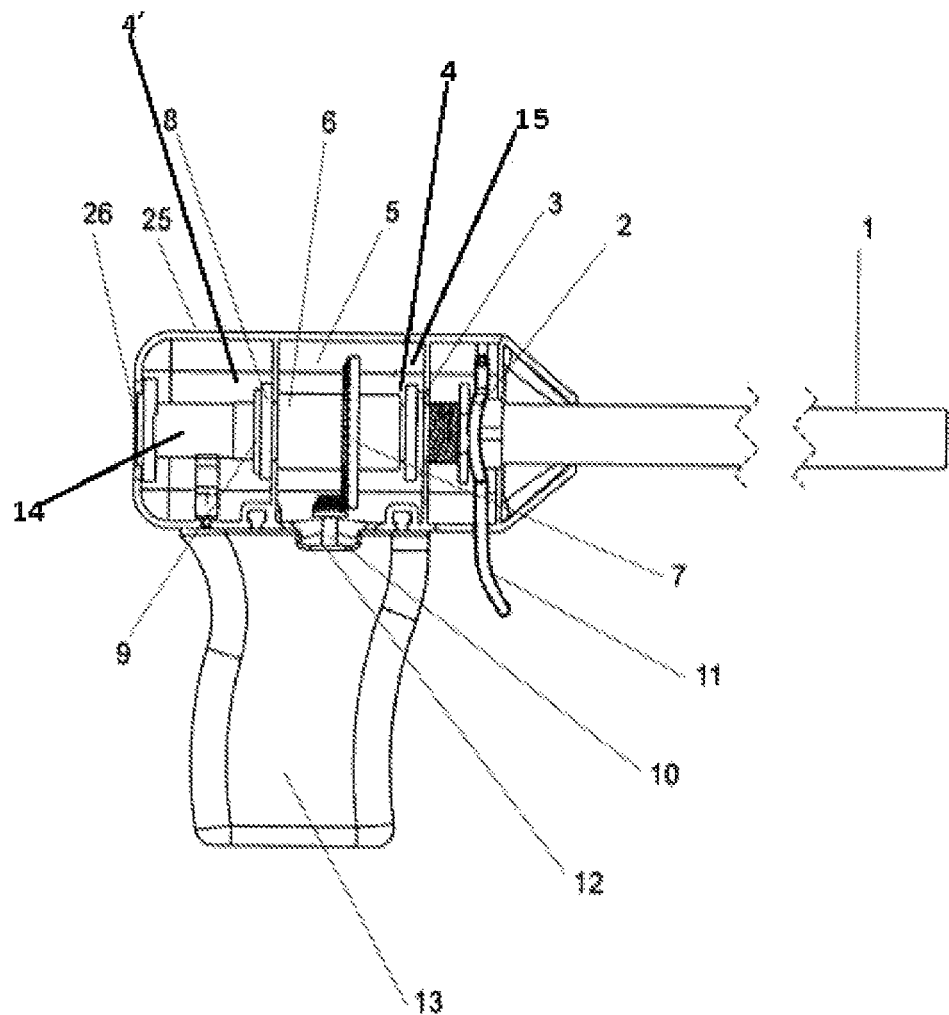
FIG. 01 is an exploded sectional view of an improved morcellator embodying the invention.
Figure 2:
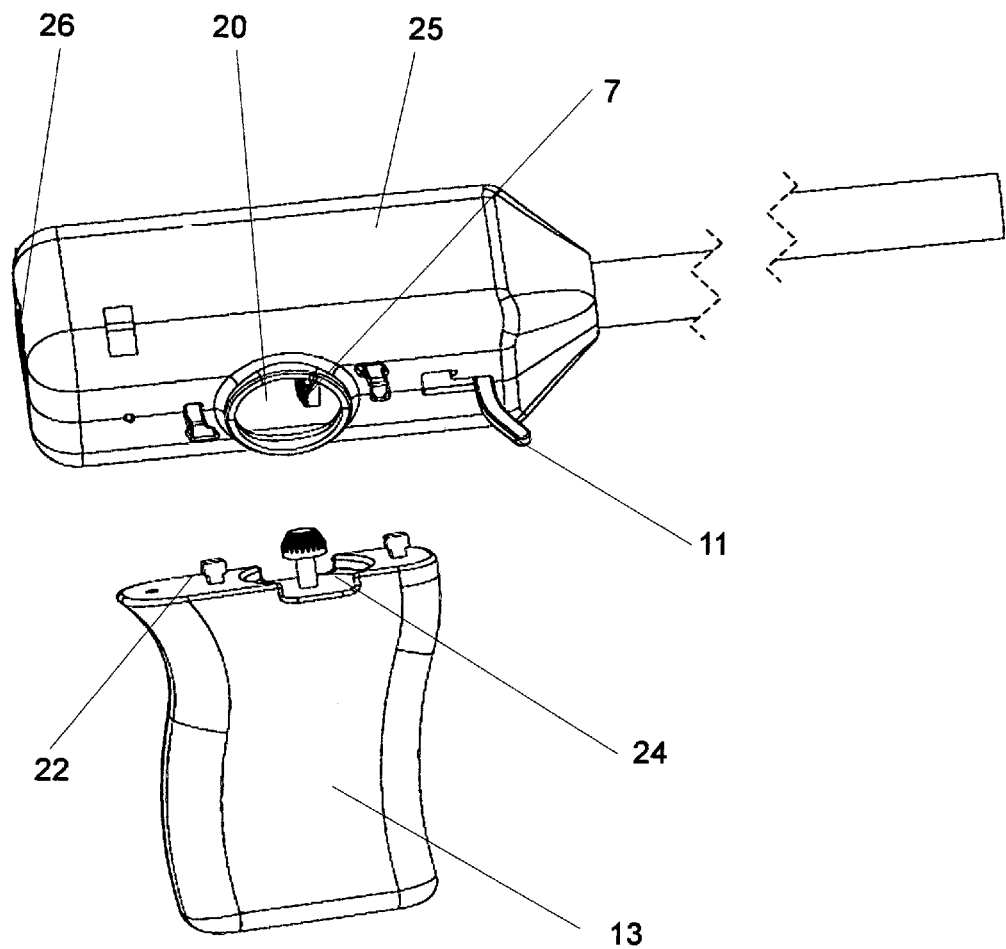
FIG. 02 is a perspective view of a cutter assembly.
Figure 3:
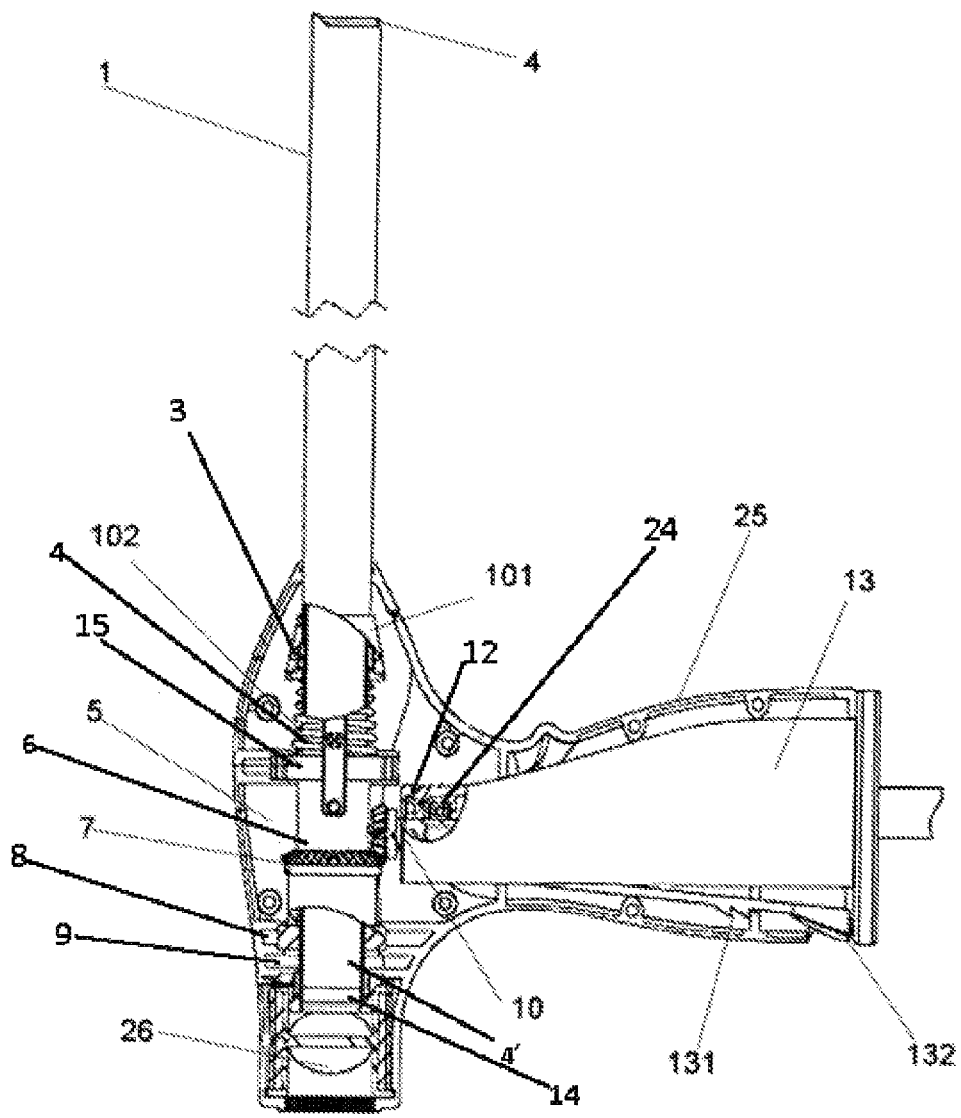
FIG. 03 is an enlarged sectional view of FIG. 01.
Figure 4:
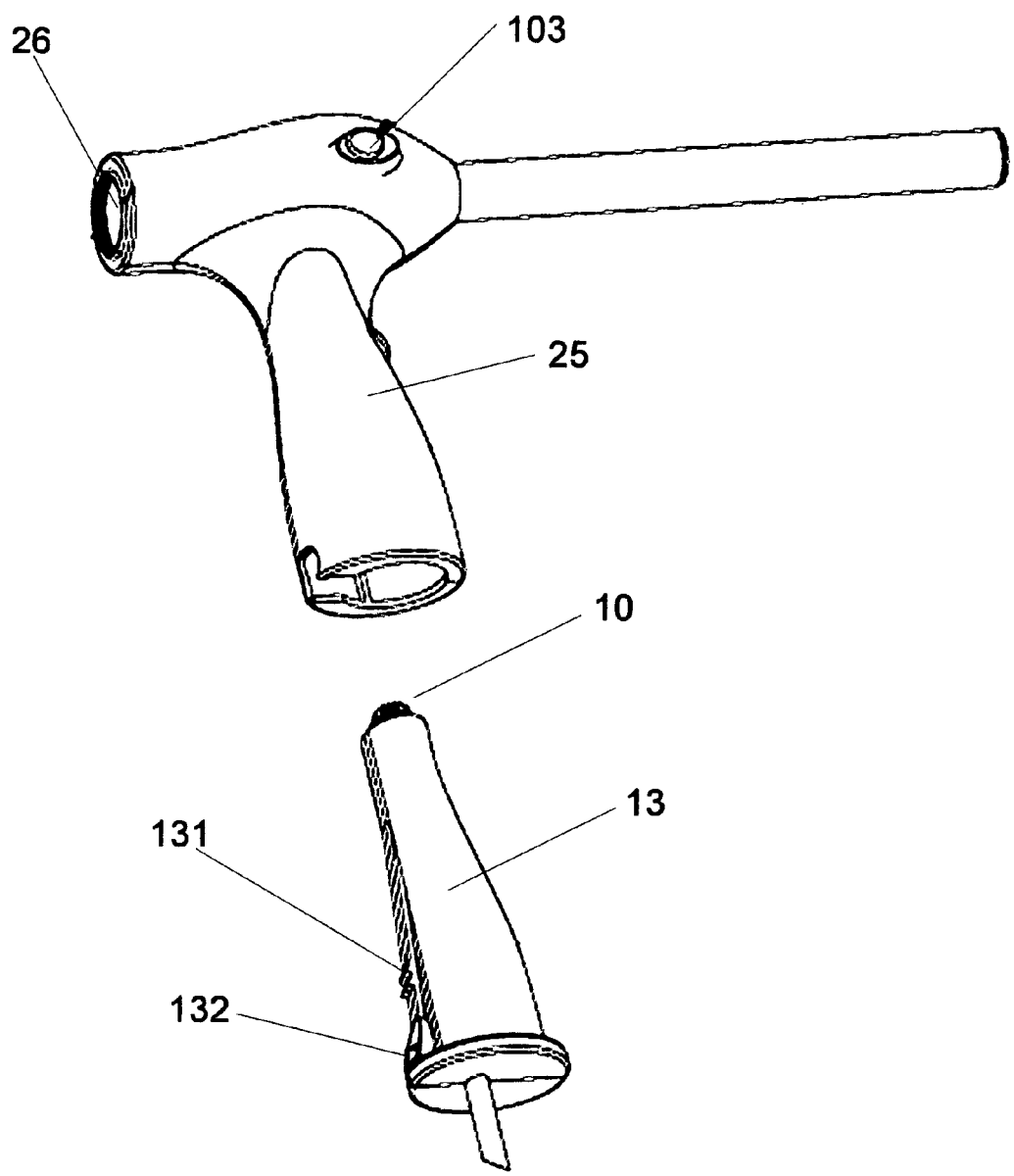
FIG. 04 is a perspective view of a cutter activation mechanism and a reusable drive assembly.

The improved morcellator of the present invention includes a rotary tissue cutting tube 04 which passes through outer sheath tube as illustrated in FIG. 01 and FIG. 03, which is driven by a cutter gear mechanism of a cutter assembly 25 as shown in FIG. 02 and FIG. 04. The morcellator comprises a disposable cutter assembly and a reusable drive assembly. The outer sheath 01 prevents surrounding tissue damage while the tissue cutting tube 04-04' rotates. There is a gap between outer sheath tube 01 and rotary tissue cutting tube 04-04' at distal end 04. Body fluids such as blood may seep through this space into the cutting assembly 25. If this fluid follows in and gets in contact with the drive gear mechanism mounted on the reusable drive assembly 13, it may pass infection from one patient to another, as it is reusable. To avoid infection from transmitting to drive assembly 13, a hydraulic seal 03 is provided on the distal portion of shaft of the cutting assembly 25. The seal 03 prevents the body fluids from getting into the sterile region of the cutter assembly 25. There are chances of body fluid going inside the inner gap of tissue cutting tube 04-04' and the outer sheath tube 01 into the sterile region of the drive assembly 13 and the sterile region of the cutter assembly 25. Therefore, the hydraulic seal 03 is located on the distal portion of the shaft of the cutting assembly 25.

The body fluid may also seep through the gap between the proximal end 04' of the tissue cutting end 04-04' and inner tube 14 and pneumatic valve 26 into the sterile region at the proximal end. To prevent body fluid seep into sterile region, a hydraulic seal 09 is provided on the proximal portion of shaft of the cutting assembly 25. Due to the seal, the sterile region remains sterile during the use of the morcellator. The morcellator may terminate directly at the pneumatic seal. Hydraulic seal 12 is attached below the pinion gear 10 in the drive gear mechanism, as shown in FIGS. 01 and 03, to prevent transmission of the infection in the drive gear mechanism. Seal 03 prevents seepage into the gaps of the outer sheath tube 01 and rotary tissue cutting tube 04-04' from patient's side at distal end and seal 09 prevents seepage into the gaps of the rotary tissue cutting tube 04-04' and inner tube 14 at proximal end 04' from surgeon's side and pneumatic valve 26 from surgeon's side in cutter driven mechanism. A seal attached before and after said cutter driven mechanism in alignment with the bearing 15 on proximal end and bearing 08 at distal end of cutter drive mechanism prevents transmission of an infection and/or body fluid seepage from surgeon's side as well as patient's side respectively. The tubes are placed in twin tube manner such that the outer sheath tube 01, rotary tissue cutting tube 04-04' and inner tube 14 are not placed consecutively together.

Another hydraulic seal 12 is mounted below the pinion gear 10 in the reusable drive assembly 13 in the drive gear mechanism. Though the drive gear mechanism is not supposed to get contaminated, in unlikely event, the infection is prevented from seeping into the body of drive assembly with the said hydraulic seal 12. The distal and proximal end of the cutter assembly 25 is sealed onto the body of drive assembly 13 thereby preventing infection transfer from drive assembly 13 to the cutter assembly 25. The hydraulic seal 12 is provided to prevent seepage of body fluid below the pinion gear 10 in the drive gear mechanism of the reusable drive assembly 13. The hydraulic seal 12 is present in alignment with the bearing 24 in the reusable drive assembly 13 as shown in FIG. 03.

The cutter assembly 25 is removed and disposed off after each use. The drive assembly 13 may be used more than once thereby saving material, environment and healthcare cost.

The cutter assembly of traditional morcellators consists of three tubes viz. cutter tube, outer steady sheath, and inner stabilizing sheath tube 14. The morcellator disclosed has unique twin tube design. The inner tube which is used in other traditional morcellators is eliminated completely. Thus new design eliminates the seeping region, between, the tissue cutting tube 04-04' and inner stabilizing sheath tube 14.

The tubes are placed in twin tube manner such that the outer sheath tube 01, tissue cutting tube 04-04' and inner tube 14 as shown in FIG. 01 are not placed consecutively together. Another advantage of twin tube over the conventional design using three tubes is that in the twin tube design, the inside space is increased as there is no tube inside the cutter tube unlike conventional morcellator design that consist of three tubes. In addition to this advantage of more space that is available for removal of tissues, twin tube provides less space for fluid seepage, aiding in keeping the device sterile. Further reducing number of component reduces material, cost and weight of the morcellator, thus increasing overall effectiveness, efficiency of the device.

Figure 6:
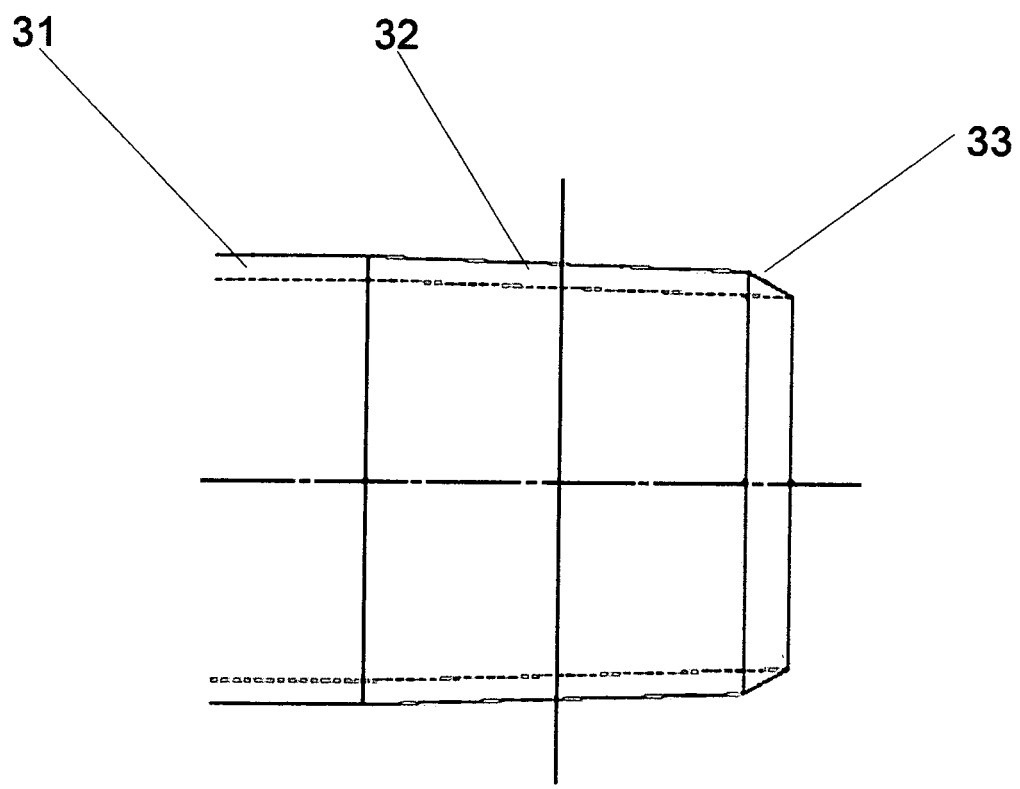
FIG. 06 is a schematic of a tissue cutting tube in one embodiment.
Figure 7:
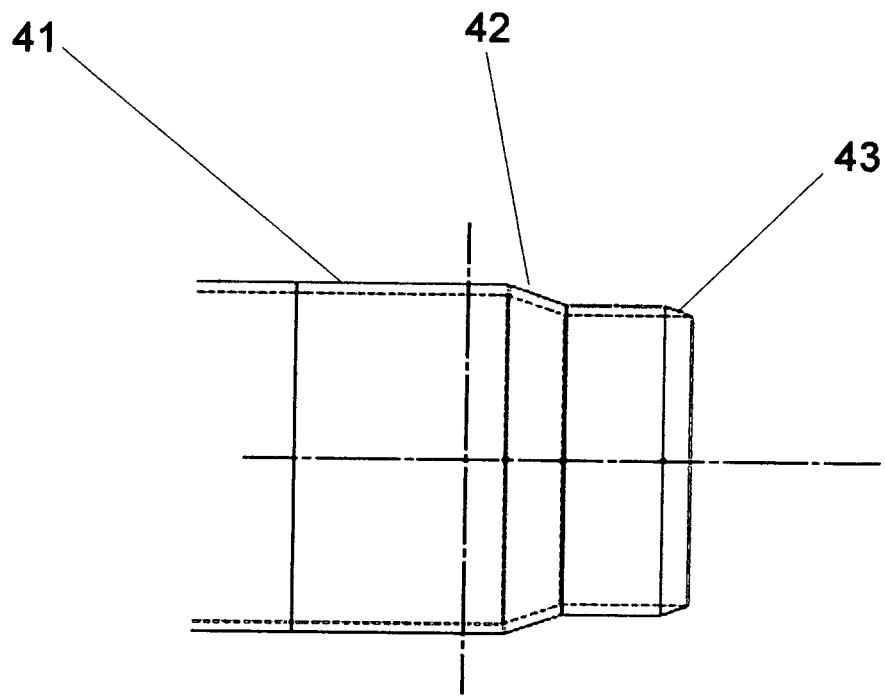
FIG. 07 is a schematic of a tissue cutting tube in another embodiment.

Cutter tube at the proximal end of the cutter assembly 25 is shown as 04' at the proximal end and as 04 at the distal end which is a single tube as shown in FIGS. 01 and 03. The tissue cutting tube 04-04' is mounted in alignment to the two bearings 08 at proximal end of the cutter assembly 25 and 15 at distal end of cutter assembly 25 respectively as shown in FIGS. 01 and 03 which are mounted on the two halves of cutter assembly 25 at the proximal end and distal end. Distal hydraulic seal 03 and proximal hydraulic seal 09 are present in alignment with the bearing 15 at distal end and bearing 08 at proximal end respectively of cutter assembly 25 as shown in FIGS. 01 and 03. Cutter driven mechanism which is in the handpiece body 5 of the cutter assembly 25 has a cutter tip 32 and 42 as shown in FIGS. 06 and 07. This cutter tip is mounted on the tissue cutting tube 04-04'. To rotate the tissue cutting tube at distal end 04 and at proximal end 04', a bevel gear 07 is mounted on a sleeve 06 which in turn is welded to the tissue cutting tube 04-04' as shown in FIGS. 01 and 03. This bevel gear 07 is meshed with pinion 10. There is an opening 20 in hand piece 05 for pinion gear 10 to engage in bevel gear 07 as shown in FIG. 02. The cutter drive mechanism can be interpreted as the cutter driven mechanism in the illustrations.

There is a trigger 11 to actuate the cutting tip 32 and 42 as well as tissue cutting tube 04-04' as shown in FIGS. 01, 06 and 07. Spring 102 is provided for the cutter mechanism. This complete assembly is disposable cutter assembly 25 as shown in FIGS. 01, 02 and 03.

Figure 5:
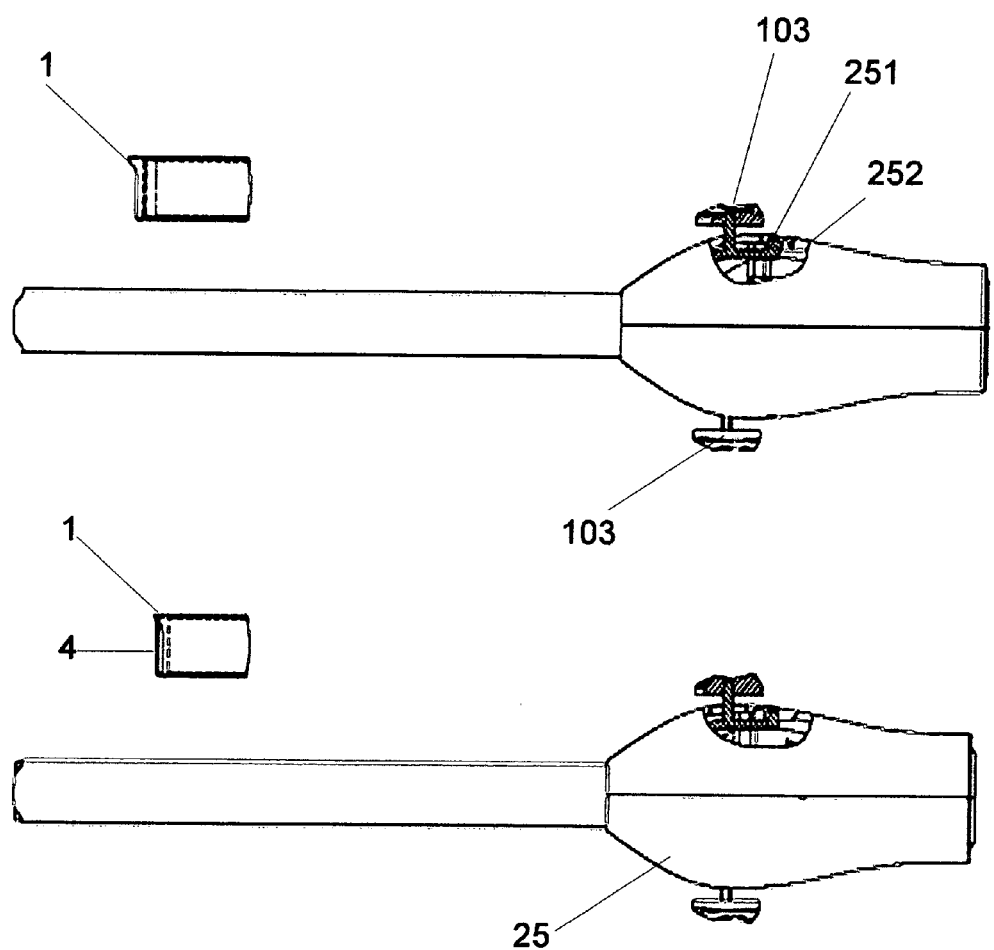
FIG. 05 is a perspective view of a cutter activation mechanism.

In the drive mechanism, the buttons 103 for cutter activation mechanism causes the rotation of the activation knob locks which exposes the tissue cutting tube 04-04' at the distal end 04 to the tissue. This kind of activation mechanism prevents unintentional and accidental exposure of the tissue cutting tube 04-04' at distal end 04 until the buttons 103 are used which causes pull collar 101 to lock in two locking positions 251, 252 which covers the tissue cutting tube 04-04' and exposes the tissue cutting tube 04-04' respectively when required as shown in FIG. 03 and FIG. 05. The bevel gear 7 is rotated by pinion gear 10 which in turn gets power from flexible shaft of rotor. This provides for the reusable drive assembly 13, as shown in FIG. 04. The one end of this flexible shaft is connected to Drive Unit which houses a DC motor.

Partial Disposing off reduces wastage of plastic and metal that leads to environmental pollution, reduces wastage and significantly bring down the cost pressure on the healthcare system.

Use of traditional cutter tube without using the inner tube may cause drag as well as twisting of the forceps. The traditional design of the cutter tube of a morcellator is uniform cylindrical. Such cutter cuts the tissue which is of the same size of the size of the Inner diameter of the cutter tube. The same size of the tissue as that of cutter tube size causes drag. A novel profile of a tissue cutting tube FIG. 06 and FIG. 07 is disclosed which produce the minimum drag during tissue removal, as the size of tissue cut by cutting edge 33 FIG. 06 and cutting edge 43 in the FIG. 07 is less than the tubes inside diameter 31 in FIG. 06 and inside diameter 41 in the FIG. 07.

Figure 8:
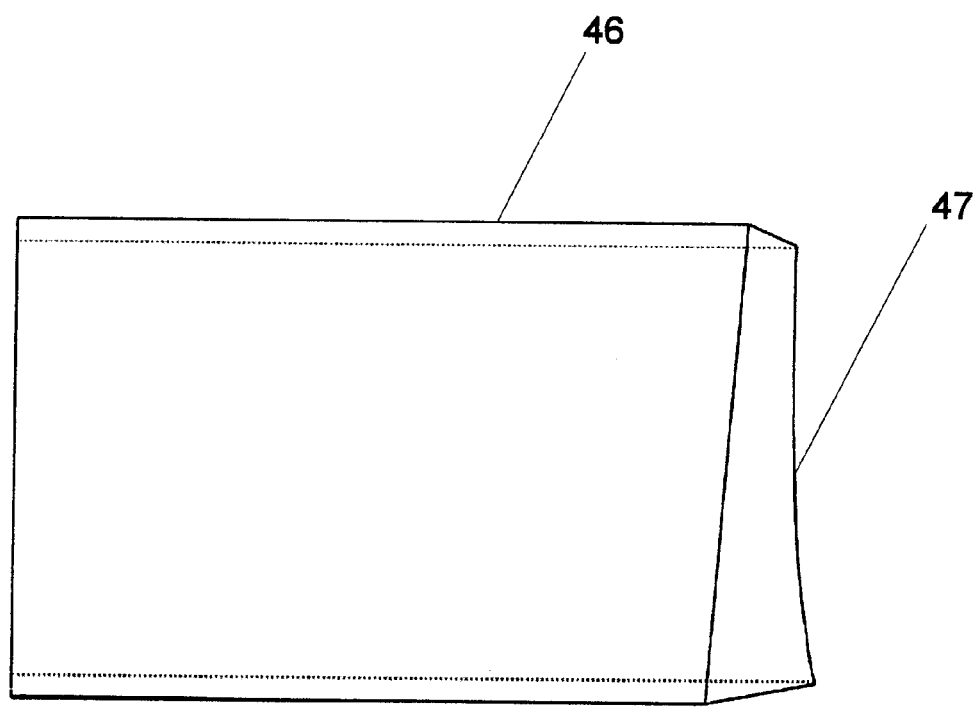
FIG. 08 is a schematic of a tissue cutting tube in another embodiment.

In traditional designs, cutting edge is formed by chamfering/grounding at one end of a tube. As disclosed in the design illustrated in FIG. 08, double shear angle 47 is given to the rotary tissue cutting tube. The cutting tube 46 is ground at one end to form the cutting edge with double shear angle. This second shear angle is achieved by cutting the ground/chamfer edge in variable plane. Due to this double shear angle 47, tissue get morcellated with less force than that required using traditional morcellator cutter.

A Cutter activation mechanism and safety lock to avoid unintentional cutter exposure is disclosed as illustrated in FIG. 04 and FIG. 05. The morcellator cutting tube is exposed by moving the outer sheath tube 01 towards proximal end.

The design of a cutter activation mechanism, shown in FIG. 05, prevents an unintentional exposure of a cutting tube 04. The outer sheath tube 01 can be moved only by activating this unique cutter tube activation mechanism as illustrated FIG. 05. The outer sheath 01 can not be moved by any other means such as a frictional force between skin and outer sheath. This is one of the safety features of the disclosed invention.

The cutter activation mechanism consists of a pull collar 101, first locking slot 251 and second locking slot 252. These locking slots are integrated in the main housing of the disposable cutter assembly 25. And pull collar 101 is attached on the outer sheath 01.

When pull collar 101 is locked in the locking slot 251, the tissue cutting tube 04-04' as shown at distal end 04 is completely covered by outer sheath 01. When pull collar 101 is locked in the locking slot 252, then the cutting edge of the tissue cutting tube 04-04' at distal end 04 is exposed. Pull collar 101 can slide by using buttons 103 provided on the main housing of the disposable cutter assembly 25 (FIG. 05). To expose the cutting edge of the tissue cutting tube 04-04', buttons 103 required to be pressed and then pulled back towards the proximal end of the device. The pull collar 101 gets locked in the locking slot 252 and so the outer sheath 01 which is attached to the pull collar 101 remains at the new position exposing the cutting edge of the tissue cutting tube 04-04'. Levers of pull collar 101 remain in the locking slot 252 even after removing the external force by removing fingers from the buttons 101 due to the spring force. In one embodiment, this spring force is provided by the springiness of the material.

The buttons 103 need to be pressed again to unlock the pull collar 101 from the locking slots 252. As pull collar 101 gets unlocked, the outer sheath 01 moves towards the distal end. Thus covers the cutting edge of a the tissue cutting tube 04-04' at distal end 04. The outer sheath 01 moves forward after unlocking the pull collar 101 as the outer sheath 01 is mounted with spring load.

The buttons 103 are placed on the both sides of the main housing of the cutter assembly 25 (FIG. 04 and FIG. 05). Both these buttons 103 need to be operated simultaneously in order to activate the cutter that is to expose the cutting edge of cutter tube 04. This eliminates the unintentional opening or closing of a cutter tube 04 by movement of outer sheath 01.

A quick engage and quick release mechanism for morcellator is further disclosed as illustrated in FIG. 03 and FIG. 04. In one of the embodiment, a novel quick engage & quick release mechanism is a single piece mechanism. It is integrated with the main housing of the reusable drive assembly.

The disposable cutter assembly 25 can be detached from the reusable drive assembly 13 by pressing a lever 132 which is integrated in the reusable drive assembly 13. This integrated lever 132 is integrated at the bottom rear side of the reusable drive assembly 13. When the disposable cutter assembly 25 is attached to the reusable drive assembly 13, the integrated lever 132 of the reusable drive assembly 13 gets concealed. This eliminates accidental activation of integrated lever 132 of the reusable drive assembly 13 and thus eliminates unintentional release of the disposable cutter assembly 25 from the reusable drive assembly 13. This integrated lever 132 can be activated by using index finger.

The reusable drive assembly 13 which drives the cutter tube 04 can be simply inserted into the disposable cutter assembly 25. The integrated lever 132 has protrusions 131 on it to enable correct positioning of the reusable drive assembly 13 into the reusable cutter assembly 25. The integrated lever 132 of the reusable drive assembly 13 itself retracts during insertion. When the reusable drive assembly 13 comes to the predetermined position inside the disposable cutter assembly 25, the integrated lever 132 retracts back to its original position. The protrusions 131 on the integrated lever 132 gets lock in the disposable cutter assembly 25.

To release the disposable cutter assembly 25 from the reusable drive assembly 13, the integrated lever 132 has to be operated. The integrated lever 132 can be manually operated by pressing with the help of an index finger.

It further disclosed the designs of unique valves used in the morcellator. In a normal working condition, the tissue cut is pulled out with the help of forceps. The forceps inserted from the proximal end of the cutter assembly. During such insertion of forceps, inflation gas escapes from the open space around the forceps. It is necessary to design a valve which will provide positive sealing however is essential to keep the minimum drag on the forceps to remove the tissue with minimum resistant to the operator.

Figure 9:
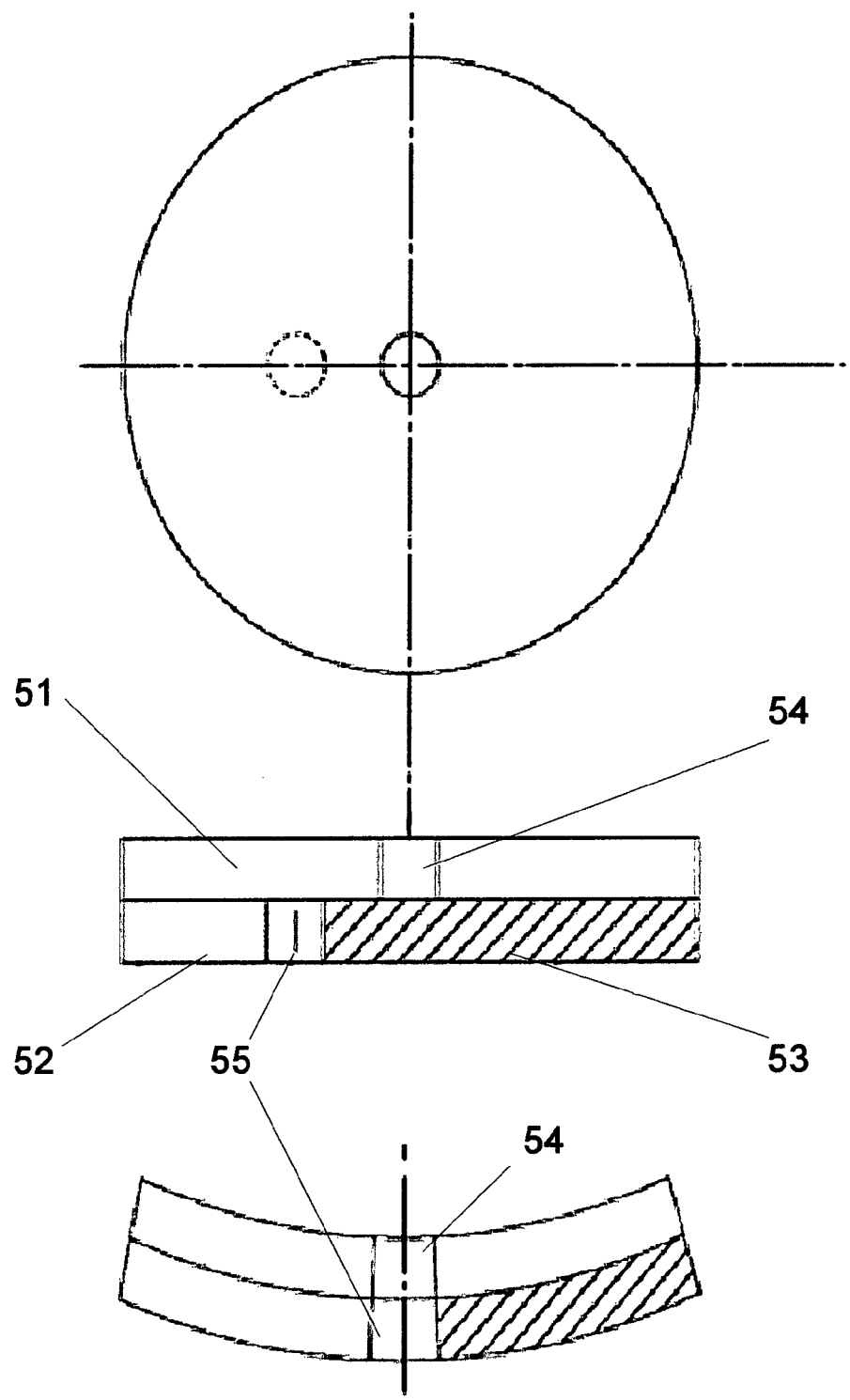
FIG. 09 is a sectional view of a valve in one embodiment.

The disclosed design of a valve FIG. 09 is unique in construction and principal. The valve greatly reduces the unintentional leakage of $CO_2$. The unique design of this valve provides the greater sealing capacity.

The valve consists of two membranes 51 and 52. Upper Membrane 51 is made up of single material and has uniform elasticity. Lower membrane 52 is partly made up of composite/fused material that has variable elasticity and partly made up of a non-elastic material.

The valve 26 is present on the proximal end of the handpiece body 05. The valve 26 is resent on the proximal end of the disposable cutter assembly 25 as shown in FIG. 03. The forceps are inserted inside the valve 26, after the morcellator is inserted into the patient's body. The presence of the valve 26 prevents unintentional leakage of $CO_2$ and also during insertion of forceps inflation gas escapes from the space around the forceps. The valve 26 consists of two membranes 51, 52. Upper membrane 51 is made up of single material and has uniform elasticity. When not in operation, the valve 26 remains in the closed dose position, whereas when in operation the valve 26 opens by aligning the gates 54 and 55 on membranes 51 and 52 respectively, FIG. 09. Thus, in one embodiment, a feature of the valve 26 has the lower membrane 52 being a composite/fused material of variable elasticity and partly made of non-elastic material 53. When an instrument is inserted through the gate 54, the elastic material of the second membrane will stretch and push, thus causing the alignment of gates 54, 55 and allowing the passage of the instrument. The alignment of gates 54, 55 will thus allow proper sealing mechanism.

Figure 10:
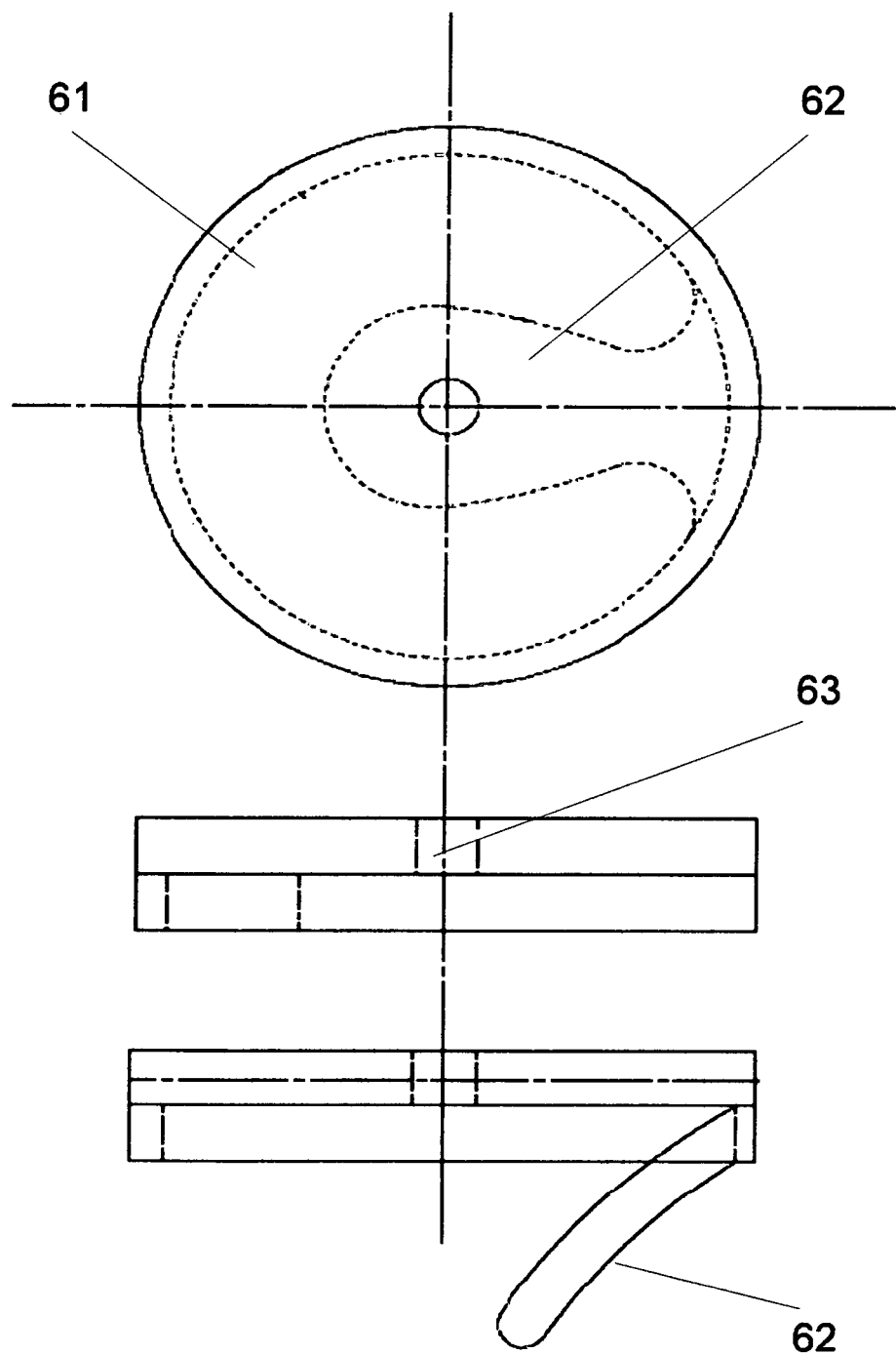
FIG. 10 is a sectional view of a valve in another embodiment.

Another embodiment of the valve design is disclosed in FIG. 10. The novel design is unique in construction. It is designed to remain close in normal condition. It consists of two membranes 61 and 62. Upper membrane 61 has a gate 63 at the centre which is covered by lower membrane 62, thus provides sealing. When tools are inserted through the gate 63 of upper membrane 61, it further pushes the lower membrane 62 which opens the valve.

Figure 11:
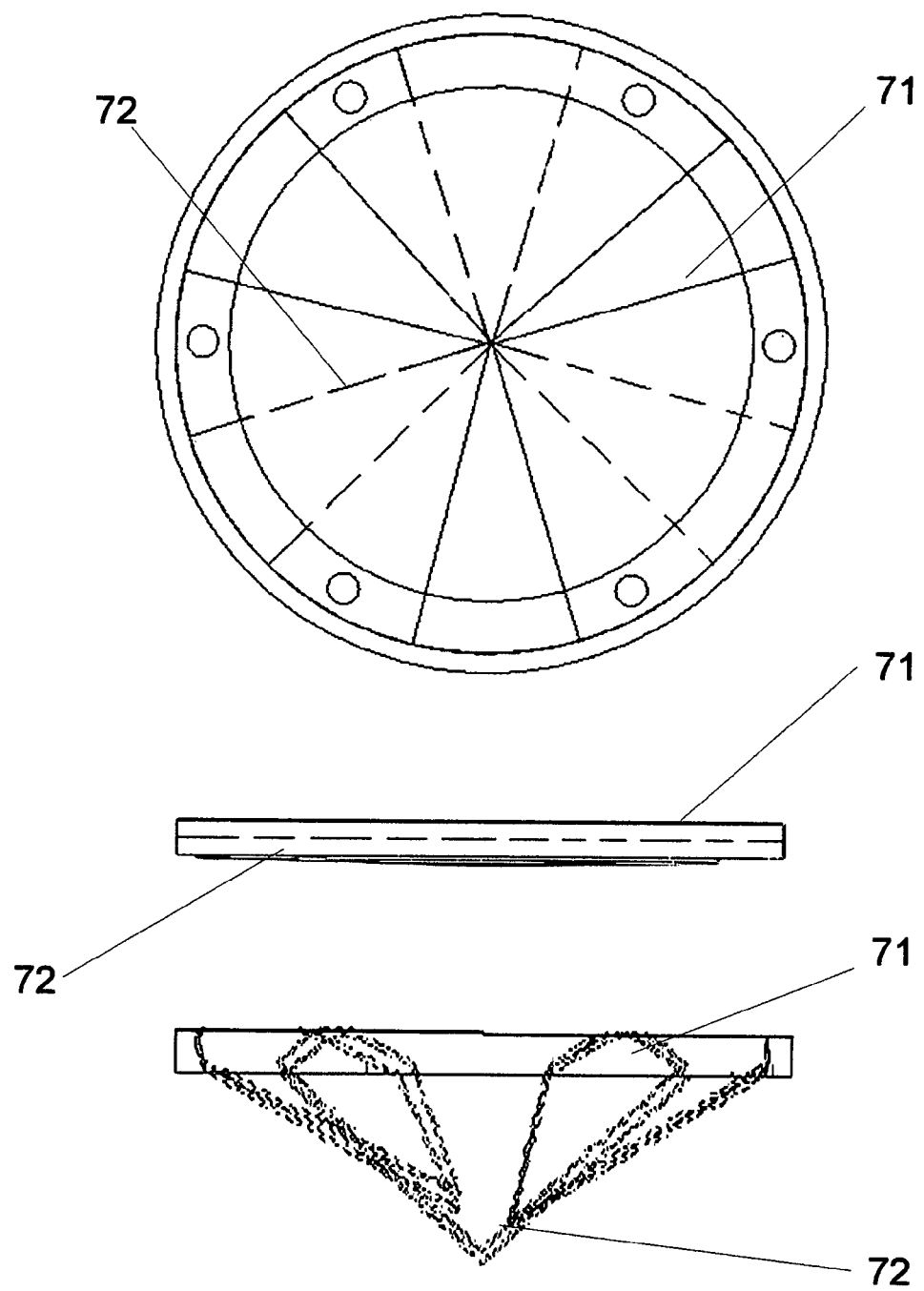
FIG. 11 is a sectional view of a valve in another embodiment.

Yet another embodiment of valve design is disclosed as illustrated in FIG. 11. This novel design comprises of number of membranes placed with each other at two different levels i.e. upper level 71 and lower level 72. The membranes provide sealing while in operation by minimizing all possible gaps between an instrument and membranes. The unique construction of small individual membranes also exerts very low drag on the instrument while removing the tissue as compare to the drag exist while operating with traditional valves.

In the foregoing description, the method and device of the present invention have been described with reference to preferred embodiments. It is to be understood and expected that variations in the principles of the method and device herein disclosed may be made by one skilled in the art and it is intended that such modifications, changes, and substitutions are to be included within the scope of the present invention as set forth in the appended claims (if any are included). The specification and the drawings are accordingly to be regarded in an illustrative rather than in a restrictive sense.

The invention claimed is:

1. A morcellator for morcellating tissue from a patient's body comprising:
   (a) a disposable cutter assembly comprising,
      a rotary tissue cutting tube, said rotary tissue cutting tube comprising variable diameter;
      a cutter driven mechanism;
      a seal attached before and after the cutter driven mechanism,
      wherein the seal maintains a sterile region around the cutter driven mechanism that prevents infection and body fluid seepage into gaps of an outer sheath tube and the rotary tissue cutting tube from a patient's side and that prevents seepage into gaps of the rotary tissue cutting tube and an inner tube from a surgeon's side;
   (b) a reusable drive assembly comprising,
      a drive gear mechanism;
      a seal attached below a pinion gear, wherein the seal prevents contamination by transmission of an infection and a body fluid to the drive gear mechanism and prevents seepage of body fluid in the drive gear mechanism; and
      an integrated lever, wherein the integrated lever has protrusions which enable locking in the disposable cutter assembly.

2. The morcellator according to claim 1, wherein the variable diameter of the rotary tissue cutting tube comprises an arrangement with a diameter of an extreme distal end of the rotary tissue cutting tube being lesser than a diameter of an inner region that is away from the extreme distal end of the rotary tissue cutting tube enabling minimum drag during tissue removal.

3. The morcellator according to claim 1, wherein the seal comprises alignment of the seal with a bearing at proximal and distal ends of the drive mechanism allows holding of the disposable cutter assembly to rotate in fixed position while maintaining alignment and preventing seepage into gaps in the disposable cutter assembly.

4. A morcellator for morcellating tissue from a patient's body comprising:
   (a) a disposable cutter assembly comprising,
      a rotary tissue cutting tube, said rotary tissue cutting tube comprising variable diameter;
      a cutter driven mechanism;
      a seal attached before and after the cutter driven mechanism; and
      a valve having a first membrane and a second membrane, wherein the valve provides low drag on forceps during tissue removal from a patient's body and reduces leakage of $CO_2$,
      wherein the seal maintains a sterile region around the cutter driven mechanism that prevents infection and body fluid see seepage into gaps of an outer sheath tube and the rotary tissue cutting tube from a patient's side and that prevents seepage into gaps of the rotary tissue cutting tube and an inner tube from a surgeon's side;
   (b) a reusable drive assembly comprising,
      a drive gear mechanism;
      a seal attached below a pinion gear, wherein the seal prevents contamination by transmission of an infection and a body fluid to the drive gear mechanism and prevents seepage of body fluid in the drive gear mechanism; and
      an integrated lever, wherein the integrated lever has protrusions which enable locking in the disposable cutter assembly.

5. The morcellator according to claim 4, wherein the first membrane of the valve is single material with uniform elasticity.

6. The morcellator according to claim 5, wherein the first membrane of the valve is single material with uniform elasticity and the second membrane of the valve is partly a composite or fused material with variable elasticity, wherein the second membrane of the valve will stretch and push from the first membrane of the valve to cause alignment of gates to allow passage of an instrument.

7. The morcellator according to claim 4, wherein the second membrane of the valve is partly a composite or fused material with variable elasticity.

8. The morcellator according to claim 7, wherein the first membrane of the valve is single material with uniform elasticity and the second membrane of the valve is partly a composite or fused material with variable elasticity, wherein the second membrane of the valve will stretch and push from the first membrane of the valve to cause alignment of gates to allow passage of an instrument.

9. The morcellator according to claim 4, wherein the first membrane of the valve is single material with uniform elasticity and the second membrane of the valve is partly a composite or fused material with variable elasticity, wherein the second membrane of the valve will stretch and push from the first membrane of the valve to cause alignment of gates to allow passage of an instrument.

* * * * *